United States Patent [19]

Hall et al.

[11] Patent Number: 4,752,616
[45] Date of Patent: Jun. 21, 1988

[54] ARYLTHIOALKYLPHENYL CARBOXYLIC ACIDS, COMPOSITIONS CONTAINING SAME AND METHOD OF USE

[75] Inventors: Steven E. Hall, Ewing Township, Mercer County; Philip D. Stein, Hopewell, both of N.J.

[73] Assignee: E. R. Squibb & Sons, Inc., Princeton, N.J.

[21] Appl. No.: 67,199

[22] Filed: Jun. 29, 1987

[51] Int. Cl.$^4$ .................. C07C 149/40; A61K 31/215
[52] U.S. Cl. ..................... 514/510; 514/533; 514/539; 514/544; 514/562; 514/569; 514/570; 560/9; 560/10; 560/11; 560/12; 560/18; 562/426; 562/427; 562/429; 562/430; 562/432
[58] Field of Search ............. 560/9, 10, 11, 12, 18; 562/426, 427, 429, 430, 432; 514/533, 539, 544, 562, 569, 570, 510

[56] References Cited

U.S. PATENT DOCUMENTS

| | | | |
|---|---|---|---|
| 3,385,886 | 5/1968 | Nicholson | 560/9 |
| 3,600,437 | 8/1971 | Marshall | 560/9 |
| 3,824,274 | 7/1974 | Franke | 560/11 |
| 3,825,587 | 7/1974 | Diamond | 560/11 |
| 3,845,089 | 10/1974 | Henrick | 560/9 |
| 3,880,916 | 4/1975 | Dickel | 560/9 |
| 4,074,057 | 2/1978 | Kaukematsu | 560/9 |
| 4,258,058 | 3/1981 | Witte et al. | 424/309 |
| 4,443,477 | 4/1984 | Witte et al. | 424/319 |

FOREIGN PATENT DOCUMENTS 56172 7/1982 European Pat. Off. .

Primary Examiner—Michael L. Shippen
Attorney, Agent, or Firm—Lawrence S. Levinson; Burton Rodney

[57] ABSTRACT

Arylthioalkylphenylcarboxylic acids are provided which have the structure

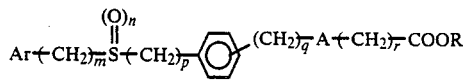

wherein Ar represents an aryl group including phenyl or naphthyl which may or may not include one or more substituents, A is

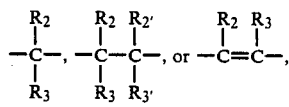

R is hydrogen, alkali metal or lower alkyl, m is 0, 1, 2, or 3, n is 0, 1, or 2, p is 1 to 5, q, is 0, 1, 2, or 3, r is 0, 1, 2, or 3. These compounds are cardiovascular agents which exhibit thromboxane antagonist activity and thus are useful in the treatment of thrombotic disease.

19 Claims, No Drawings

ARYLTHIOALKYLPHENYL CARBOXYLIC ACIDS, COMPOSITIONS CONTAINING SAME AND METHOD OF USE

FIELD OF THE INVENTION

The present invention relates to arylthioalkylphenyl carboxylic acids which are useful in the treatment of thrombotic disease.

BACKGROUND OF THE INVENTION

U.S. Pat. No. 4,258,058 discloses phenoxyalkyl carboxylic acids which inhibit thrombocyte aggregation and depress serum lipids and have the structure

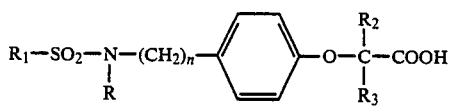

wherein

R is hydrogen or lower alkyl;

$R_1$ is an alkyl or aryl, aralkyl or aralkenyl radical, the aryl moiety of which can be substituted one or more times by halogen, hydroxyl, trifluoromethyl or lower alkyl, alkoxy or acyl;

$R_2$ and $R_3$, which can be the same or different, are hydrogen or lower alkyl and n is 0, 1, 2 or 3;

as well as the physiologically acceptable salts, esters and amides thereof.

U.S. Pat. No. 4,443,477 discloses sulphonamidophenyl carboxylic acids which inhibit thrombocyte aggregation and depress serum lipids and have the structure

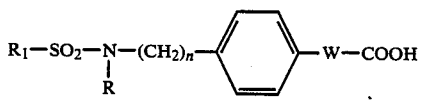

wherein

R is a hydrogen atom or a lower alkyl radical;

$R_1$ is an alkyl radical or an aryl, aralkyl or aralkenyl radical, the aryl moiety of which in each case can be optionally substituted one or more times by hydroxyl, halogen, trifluoromethyl, lower alkyl or alkoxy or by acyl, carboxy or alkoxycarbonyl;

n is 1, 2 or 3; and

W is a bond or an unbranched or branched divalent aliphatic hydrocarbon chain, which is either saturated or contains a double bond, as well as the physiologically acceptable salts, esters and amides thereof.

DESCRIPTION OF THE INVENTION

In accordance with the present invention, arylthioalkylphenyl carboxylic acid compounds are provided having the following structural formula:

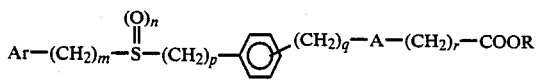

wherein

Ar represents aryl which is unsubstituted or optionally substituted with one, two or three of the following: halogen, lower alkyl, lower alkoxy, phenyl, hydroxy, alkanoyl, aroyl, alkylamino, alkoxycarbonyl or carboxy;

A is

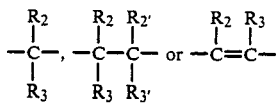

wherein $R_2$ and $R_3$, and $R_{2'}$ and $R_{3'}$, may be the same or different and are independently selected from hydrogen or lower alkyl, R is hydrogen, alkali metal (such as Na, K or Li) or lower alkyl, n is 0, 1 or 2, m is 0, 1, 2 or 3, p is 1 to 5, q is 0, 1, 2 or 3, and r is 0, 1, 2 or 3.

The $(CH_2)_m$, $(CH_2)_p$, $(CH_2)_q$ and $(CH_2)_r$ groups may be optionally substituted with one or two lower alkyl and/or one or two lower alkoxy substituents.

The $-(CH_2)_q-A-(CH_2)_r-COOR$ group may be attached at the ortho, meta or para position, with para being preferred.

Thus, the compounds of the invention include the following types of compounds.

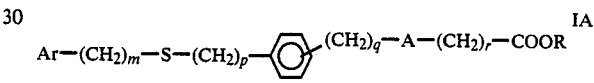  IA

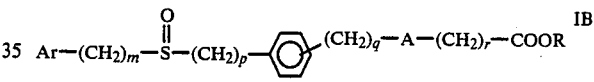  IB and

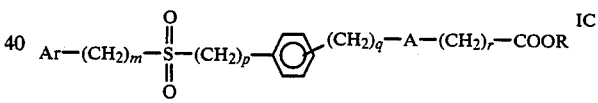  IC

The term "lower alkyl" or "alkyl" as employed herein by itself or as part of another group includes both straight and branched chain hydrocarbon radicals of up to 12 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including one or two halo-substituents, such as F, Br, Cl or I or $CF_3$, an alkoxy substituent, an aryl substituent, an alkyl-aryl substituent, a haloaryl substituent, a cycloalkyl substituent or an alkylcycloalkyl substituent.

The term "cycloalkyl" by itself or as part of another group includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogens, 1 or 2 lower alkyl groups and/or 1 or 2 lower alkoxy groups.

The term "aryl" or "Ar" as employed herein by itself or as part of another group refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be 1 or 2 lower alkyl groups, 1 or 2 halogens (Cl, Br or F), and/or 1 or 2 lower alkoxy groups, or one or more of phenyl, hydroxy, alkanoyl, aroyl, alkoxycarbonyl or carboxy.

The term "aralkyl", "aryl-alkyl" or "aryl-lower alkyl" as used herein by itself or as part of another group refers to lower alkyl groups as discussed above having an aryl substituent, such as benzyl.

The term "alkanoyl" and "aroyl" refer to a lower alkyl group linked to a carbonyl group or an aryl group linked to a carbonyl group.

The term "halogen" or "halo" as used herein by itself or as part of another group refers to chlorine, bromine, fluorine or iodine, with chlorine being preferred.

The terms "$(CH_2)_m$", "$(CH_2)_p$", "$(CH_2)_q$" and "$(CH_2)_r$" where present include a straight or branched chain radical having 1 to 3 carbons in the normal chain in the case of "$(CH_2)_m$", 1 to 5 carbons in the normal chain in the case of "$(CH_2)_p$" and 1 to 3 carbons in the normal chain in the case of "$(CH_2)_q$" and/or "$(CH_2)_r$" and may contain one or more lower alkyl and/or lower alkoxy substituents. Examples of $(CH_2)_m$, $(CH_2)_p$, $(CH_2)_q$ and $(CH_2)_r$ groups include $$-CH_2-, -\underset{\underset{CH_3}{|}}{\overset{\overset{CH_3}{|}}{C}}-, -\underset{\underset{C_2H_5}{|}}{CH}-, -\underset{\underset{CH_3}{|}}{CH}-, -CH_2CH_2-, -(CH_2)_3-,$$

$$-(CH_2)_4-, -(CH_2)_5-, -\underset{\underset{}{}}{\overset{\overset{OCH_3}{|}}{CH}}-CH_2-, -\underset{\underset{}{}}{\overset{\overset{CH_3}{|}}{CH}}-CH_2-$$

$$-CH_2-\overset{\overset{Cl}{|}}{CH}-, -CH_2-\underset{\underset{OCH_3}{|}}{\overset{\overset{OCH_3}{|}}{C}}-, -\underset{\underset{CH_3}{|}}{\overset{\overset{CH_3}{|}}{C}}-CH_2-, -(CH_2)_5-,$$

$$-\underset{\underset{CH_3}{|}}{CH}-, -(CH_2)_2-\underset{\underset{CH_3}{|}}{CH}-, -CH_2-\underset{\underset{CH_3}{|}}{CH}-, -(CH_2)_2-\underset{\underset{CH_3}{|}}{\overset{\overset{CH_3}{|}}{C}}-,$$

$$-CH_2-\underset{\underset{CH_3}{|}}{CH}-\underset{\underset{CH_3}{|}}{CH}-CH_2-, -CH_2-\underset{\underset{CH_3}{|}}{CH}-CH_2-\underset{\underset{CH_3}{|}}{CH}-$$

and the like.

Preferred are those compounds of the invention wherein Ar is halophenyl, such as p—Cl—$C_6H_4$—, n is 2, m is 0, $(CH_2)_p$ is $(CH_2)_3$, q is 0, r is 0, A is $CH_2$ in the para position on the benzene ring and R is hydrogen.

The various compounds of the invention may be prepared as outlined below.

Compounds of the invention where n is 0, 1 or 2 may be prepared starting with the mercaptan A $$Ar-(CH_2)_m-SH \qquad A$$

which is alkylated by treating A with a strong base such as an alkali metal alkoxide like potassium t-butoxide, sodium methoxide or sodium ethoxide and alkylating agent B or C $$Br-(CH_2)_p-\underset{}{\overset{}{\bigcirc}}-(CH_2)_q-A-(CH_2)_r-COOalkyl \qquad B$$

or $$Br-(CH_2)_p-\underset{}{\overset{}{\bigcirc}}-(CH_2)_q-A-(CH_2)_r-Pro \qquad C$$

in the presence of an inert organic solvent like tetrahydrofuran, dimethyl sulfoxide or ethanol to form the sulfide compound IIa or IIb $$Ar-(CH_2)_m-S-(CH_2)_p-\underset{}{\overset{}{\bigcirc}}-(CH_2)_q-A-(CH_2)_r-COOalkyl \qquad IIa$$

or $$Ar-(CH_2)_m-S-(CH_2)_p-\underset{}{\overset{}{\bigcirc}}-(CH_2)_q-A-(CH_2)_r-Pro \qquad IIb$$

where Pro represents a protected alcohol group such as $$-CH_2-O-\underset{\underset{CH_3}{|}}{\overset{\overset{CH_3}{|}}{Si}}-\underset{\underset{CH_3}{|}}{\overset{\overset{CH_3}{|}}{C}}-\underset{\underset{CH_3}{|}}{\overset{\overset{CH_3}{|}}{CH}}, -CH_2O\underset{\underset{CH_3}{|}}{\overset{\overset{CH_3}{|}}{Si}}-\underset{}{\overset{\overset{CH_3}{|}}{C}}-CH_3$$

$$-CH_2O\underset{\underset{}{}}{\overset{\overset{}{}}{Si}}-\underset{\underset{}{\bigcirc}}{\overset{\overset{\bigcirc}{}}{C}}\underset{\underset{CH_3}{|}}{\overset{\overset{CH_3}{|}}{}}-CH_3$$

The above reaction is carried out at a temperature within the range of from about 20° to about 80° C. employing a molar ratio of A:base within the range of from about 0.8:1 to about 3:1 and preferably from about 1:1 to about 1.5:1, and a molar ratio of B or C:A of within the range of from about 0.8:1 to about 1.2:1 and preferably from about 0.9:1 to about 1.1:1.

The sulfide IIa may be converted to compound IA of the invention (where R is H) by subjecting IIa to basic hydrolysis by treatment of IIa with a base such as lithium hydroxide, sodium hydroxide or potassium hydroxide to form the corresponding alkali metal salt, followed by neutralization with an acid such as dilute hydrochloric acid or oxalic acid to form IA.

Sulfoxide compounds of formula IB (n is 1) may be prepared by oxidizing sulfide compounds IIa or IIb employing as an oxidizing agent, such as Jones Reagent for IIb, or sodium periodate for IIa, employing a molar ratio of IIa or IIb:oxidizing agent of within the range of from about 1:1 to about 3:1 and preferably from about 1.5:1 to about 2:1 to form IB in the case of IIb or sulfoxide III in the case of IIa $$Ar-(CH_2)_m-\overset{\overset{O}{\|}}{S}-(CH_2)_p-\underset{}{\overset{}{\bigcirc}}-(CH_2)_q-A-(CH_2)_r-COOalkyl \qquad III$$

which may be subjected to basic hydrolysis as described above to form the acid IB (where R is H).

Sulfone compounds of formula IC (n is 2) may be prepared by oxidizing sulfide IIa or IIb or oxidizing sulfoxide III, as described above or oxidized using Oxone® (Dupont) employing a molar ratio of IIa or IIb:oxidizing agent of within the range of from about 2:1 to about 6:1 and preferably from about 3:1 to about 5:1 or employing a molar ratio of IB:oxidizing agent of within the range of from about 2:1 to about 4:1 and preferably from about 2.5:1 to about 3:1, to form sulfone IVb in the case of IIb or sulfone IVa in the case of IIa or III

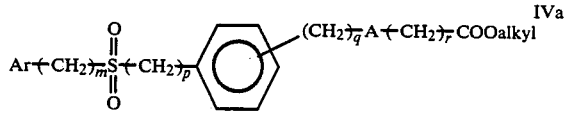

or

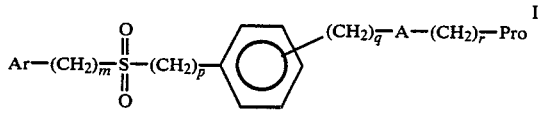

which may be subjected to basic hydrolysis as described above to form IC (where R is H).

The protected sulfone IVb is then subjected to a Jones oxidation wherein IVb is reacted with Jones reagent, namely, CrO₃ dissolved or suspended in concentrated sulfuric acid in the presence of acetone to form acid compound IC.

In an alternative process, compounds of formula I wherein n is 2 and m is 0, that is

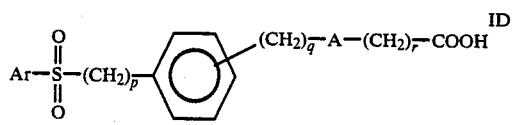

may be prepared by alkylating sulfone D

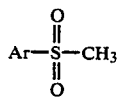

by treating a solution of D at −10° C. to 10° C. in an inert organic solvent such as tetrahydrofuran or ether with a lithiated strong base such as an alkyl lithium compound like n-butyllithium, lithium diisopropylamine or lithium bistrimethylsilylamide in an inert organic solvent such as hexane, ether or THF cooling the resulting solution to from about −80° C. to about +50° C. and reacting same with a solution of protected compound E

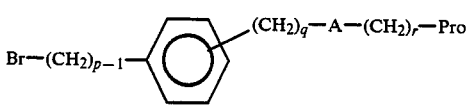

or the like in an inert organic solvent such as tetrahydrofuran or ether to form protected sulfone IVb

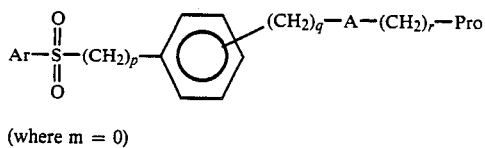

(where m = 0)

Other known alcohol protecting groups may be employed which may then be removed in a separate step prior to oxidation. The above reaction is carried out employing a molar ratio of D:base of within the range of from about 1.4:1 to about 1.05:1 and preferably from about 1.2:1 to about 1.1:1 and a molar ratio of D:E of within the range of from about 4:1 to about 1:1 and preferably 1.5:1.

The protected sulfone IVb is then subjected to a Jones oxidation wherein IVb is reacted with Jones reagent, namely, CrO₃ dissolved or suspended in concentrated sulfuric acid in the presence of acetone to form acid compound ID.

The starting material C where p is 3, 4 or 5 may be prepared starting with protected aryl bromide compound F

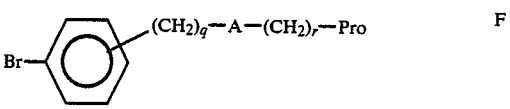

which is added to a mixture of magnesium and I₂ in an inert organic solvent such s tetrahydrofuran under an inert atmosphere such as argon to form a Grignard solution. The Grignard solution is added to a stirred solution of dibromoalkane G

and Li₂CuCl₄ in the presence of an inert organic solvent such as tetrahydrofuran and under an inert atmosphere such as argon to form C

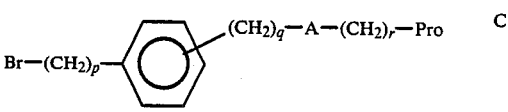

which is subjected to a Jones oxidation and esterification to form B

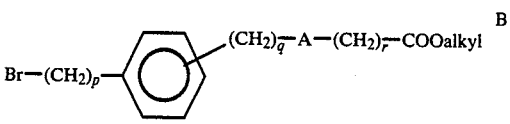

The starting compound E may be prepared starting with diol H

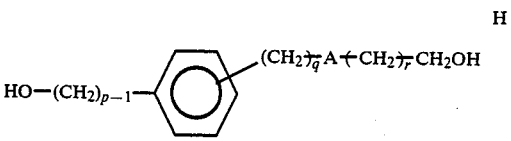

which is reacted with a protecting compound J

Cl—Prop    J (wherein Prop represents a protecting group such as

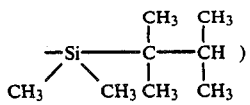

in the presence of NaH or other strong base and tetrahydrofuran or other inert organic solvent to form the protected compound K

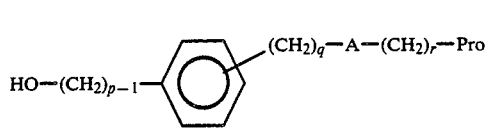

Compound K is then brominated in the presence of triphenylphosphine to form E

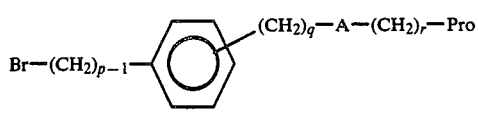

Starting compound B may also be prepared by the above-described procedure for E using diol L

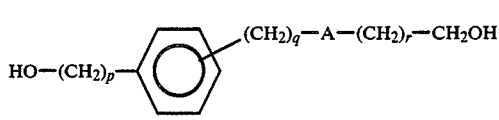

The compounds of this invention are cardiovascular agents useful as platelet aggregation inhibitors, such as in inhibiting arachidonic acid-induced platelet aggregation, e.g., for treatment of thrombotic disease such as coronary or cerebral thromboses, and in inhibiting bronchoconstriction. They are also thromboxane $A_2$ receptor antagonists, e.g., having a vasodilatory effect for treatment of myocardial ischemic disease, such an angina pectoris.

The compounds of this invention may also be used in combination with a cyclic AMP phosphodiesterase (PDE) inhibitor such as theophylline or papaverine in the preparation and storage of platelet concentrates.

The compounds of the invention can be administered orally or parenterally to various mammalian species known to be subject to such maladies, e.g., humans, cats, dogs and the like in an effective amount within the dosage range of about 1 to 100 mg/kg, preferably about 1 to 50 mg/kg and especially about 2 to 25 mg/kg on a regimen in single or 2 to 4 divided daily doses.

The active substance can be utilized in a composition such as tablet, capsule, solution or suspension containing about 5 to about 500 mg per unit of dosage of a compound or mixture of compounds of formula I. They may be compouneded in conventional matter with a physiologically acceptable vehicle or carrier, excipient, binder, preservative, stabilizer, flavor, etc., as called for by accepted pharmaceutical practice. Also as indicated in the discussion above, certain members additionally serve as intermediates for other members of the group.

The compounds of the invention may also be administered topically to treat peripheral vascular diseases and as such may be formulated as a cream or ointment.

The following Examples represent preferred embodiments of the present invention. Unless otherwise indicated, all temperatures are expressed in degrees Centigrade.

EXAMPLE 1

4-(3-((4-Chlorophenyl)sulfonyl)propyl)benzeneacetic acid

A. p-(2-Thexyldimethylsilyloxyethyl)phenethyl bromide (1) p-Thexyldimethylsilyloxyethylphenethyl alcohol To a stirred solution of 59.2% NaH slurry (4.83 g, 119 mmol) in 120 ml of dry THF under argon was added a solution of p-bis(2-hydroxyethyl)benzene (18.6 g, 119 mmol) in 85 ml of dry THF over 10 minutes. The mixture was heated at 55° C. for 3.5 hours and cooled to room temperature. To this mixture was added thexyldimethylsilyl chloride (23.5 ml, 119 mmol) dropwise over 5 minutes. The reaction mixture was stirred at room temperature for 16 hours and then poured into 1.4 l. of ether. The resulting solution was washed with saturated $NaHCO_3$ solution (3×200 ml), dried ($MgSO_4$) and filtered. The filtrate was concentrated in vacuo and chromatographed on 240 g of Merck silica gel 60 using hexane-ether 4:1 as eluant to give 10.7 g of p-(2-thexyldimethylsilyloxyethyl)phenethyl alcohol (29%). TLC: silica gel, hexane-ether 2:1, Rf 0.24, $Ce(SO_4)_2$.

(2) p-(2-Thexyldimethylsilyloxyethyl)phenethyl bromide

To a stirred solution of $(C_6H_5)_3P$ (9.03 g, 34.4 mmol) in 220 ml of toluene at 0° C. was added bromine (1.76 ml, 34.4 mmol) over 10 minutes. To this stirred slurry was then added a solution of p-(2-thexyldimethylsilyloxyethyl)phenethyl alcohol (10.6 g, 34.4 mmol) and pyridine (2.78 ml, 34.4 mmol) in 50 ml of toluene over 10 minutes. This mixture was stirred at room temperature for 4 hours and diluted with 300 ml of saturated $NaHCO_3$ solution. The resulting mixture was extracted with ether (4×300 ml). The combined ether extracts were dried ($MgSO_4$), filtered and concentrated in vacuo. The residue was triturated in 200 ml of hexane-ether 4:1 and filtered. The filtrate was concentrated and distilled under vacuum to give 9.9 g of p-(2-thexyldimethylsilyloxyethyl)phenethyl bromide (78%) as an oil.

B.

2-(4-(3-((4-Chlorophenyl)sulfonyl)propyl)phenyl)ethyl alcohol thexyldimethylsilyl ether To a 0° C. solution of (4-chlorophenyl)methyl sulfone (411 mg, 2.15 mmol) in 10 ml of dry THF was added, dropwise, n-BuLi (in hexanes, 2.5M, 0.86 ml, 2.15 mmol). After 30 minutes, the bright yellow heterogeneous solution was cooled to −78° C. A solution of Part A(2) compound (400 mg, 1.08 mmol) in THF (3 ml) was added dropwise. The reaction was then allowed to warm to room temperature. After stirring for 17 hours, water (1 ml) was added. The THF was removed in vacuo and the residue was partitioned between water (10 ml) and ether (10 ml). The aqueous phase was extracted with ether (15 ml). The combined ether layers were dried (Na$_2$SO$_4$) and concentrated in vacuo. Chromatography (flash, silica, 15 cm×25 mm, 10% ether/hexanes then 50% ether/hexanes) provided title sulfone in the form of a white solid (328.4 mg, 63% yield).

C. 4-(3-((4-Chlorophenyl)sulfonyl)propyl)benzeneacetic acid

Jones reagent was prepared: CrO$_3$ (2.67 g) was dissolved/suspended in 2.3 ml of concentrated sulfuric acid and the mixture was diluted, with cooling, to 10 ml with water. Part B sulfone (328 mg, 0.683 mmole) was dissolved in acetone (6 ml). To this solution Jones reagent (1.5 ml) was added dropwise. After 45 minutes, excess oxidant was destroyed by the addition of 2-propanol. The reaction was concentrated in vacuo. The residue was stirred with water (25 ml) until the chromium salts dissolved to form a blue solution which left a white solid in suspension. The solid was collected by filtration, washed with water and air dried. Recrystallization of this solid from ethyl acetate-hexanes provided white needles (164 mg, 68% yield.). The mother liquors yielded an additional crop of a white solid (18 mg). For the product: m.p. 178°-179° C.; R$_f$ (10% MeOH—CHCl$_3$, silica) 0.37; $^1$H NMR (270 MHz, deuteriochloroform-tetradeuteriomethanol) $\delta$ 7.81 (d, J=8.4 Hz, 2H), 7.54 (d, J=8.4 Hz, 2H), 7.20 (d, J=8 Hz, 2H), 7.06 (d, J=8 Hz, 2H), 3.57 (s, 2H), 3.05-3.19 (m, 2H), 2.69 (t, J=7.4 Hz, 2H), 1.96-2.07 (m, 2H); $^{13}$C NMR (67.88 MHz, deuteriochloroform-tetradeuteriomethanol, complete decoupling) selected peaks, $\delta$ 140.5; 138.3, 132.4, 129.6, 129.5, 129.4, 128.4, 55.3, 40.6, 33.5, 24.0; IR (nujol mull) 1701 (m), 1587 (w), 1522 (w), 1460 (m), 1410 (w), 1397 (w), 1319 (m), 1279 (w), 1258 (w), 1244 (w), 1220 (w), 1147; (s), 1086 (s), 1025 (w), 1015 (w), 917 (br, w), 837 (w), 826 (w), 790 (w), 773 (m), 749 (w), 740 (w) cm$^{-1}$; LRMS (CI, CH$_4$/N$_2$O DEP, neg. ion spectrum) m/z (rel. int.) 355 (12), 354 (37), 353 (36), 352 (100), 317 (9), 316 (8).

Anal calcd for C$_{17}$H$_{17}$ClO$_4$S: C, 57.87; H, 4.86; Cl, 10.05; S, 9.09; Found: C, 57.83; H, 4.93; Cl. 10.13; S, 9.28.

EXAMPLE 2

Methyl 4-(3-(((4-Chlorophenyl)methyl)thio)propyl)benzeneacetate

A. 3-(4-(2-(Thexyldimethylsilyloxy)ethyl)phenyl)propyl bromide

To a stirred mixture of Mg (7.00 g, 0.29 mol) and I$_2$ (one crystal) in 70 ml of dry THF under argon at 30° C. was added dropwise 10% of a solution of p-(2-(thexyldimethylsilyloxy)ethyl)phenyl bromide (50 g, 0.14 mol) in 10 ml of dry THF. This mixture was stirred vigorously and the I$_2$ color disappeared in 5 minutes. The remaining THF solution of bromide was added dropwise over 15 minutes. The mixture was heated at 40° C. for one hour and cooled to room temperature. To a stirred solution of 1,3-dibromopropane (18 ml, 0.18 mol) and 0.1M solution of Li$_2$CuCl$_4$ in THF (28 ml, 2.8 mmol) in 50 ml of dry THF under argon at 0° C. was added the above Grignard solution at a rate such that the pot temperature did not exceed 7° C. An additional 110 ml of dry THF was used to rinse in the residue of the Grignard reagent. The addition on this scale took 70 minutes. Thee reaction mixture was stirred at 0° C. for one hour and 2 hours at room temperature. The reaction mixture was cooled to 0° C. and quenched by dropwise addition of 30 ml of CH$_3$OH over 5 minutes. The mixture was concentrated in vacuo and partitioned between saturated NH$_4$Cl solution (800 ml) and ether (3×800 ml). The combined ether extracts were dried (MgSO$_4$), filtered and concentrated in vacuo. The crude product was subjected to bulb to bulb distillation under vacuum to give 37.8 g (68%) of title bromide. TLC: silica gel, hexane-benzene 1:1, R$_f$ 0.86, Ce(SO$_4$)$_2$.

B. Methyl 4-(3-Bromophenyl)benzeneacetate

To a 0° C. solution of Example 2 Part A halide (2.0 g, 5.19 mmol) in acetone (50 ml) was added, dropwise, freshly prepared Jones Reagent (ca. 3 ml. 2.67M). The reaction was stirred for 20 minutes after the addition was complete. Excess oxidant was destroyed with 2-propanol (ca. 5 ml). The mixture was concentrated in vacuo to a volume of ca. 20 ml. Water (50 ml) was added and the green mixture was extracted with ether (4×50 ml). The combined ether layers were concentrated in vacuo. The residue was triturated with petroleum ether (30°-60°) until the washings were colorless. The resultant solid (530 mg, 40%) was then taken up in methanol and esterified with an excess of ethereal diazomethane to provide title ester (530 mg, 38%). The petroleum ether triturant contained additional, however impure, acid product. The petroleum ether was removed in vacuo and the residue was esterified as above. This crude ester was taken up in petroleum ether and filtered to remove insoluble material. The filtrate was concentrated in vacuo and chromatographed (flash, silica, 15 mm dia., 10% ethyl acetate/hexanes) to yield additional title ester (197 mg, 14%): $^1$H NMR (deuteriochloroform, 60 mHz) $\delta$ 7.17 (s, 4H), 3.67 (s, 3H), 3.57 (s, 2H), 3.36 (t, J=6 Hz, 2H), 2.53-2.90 (m, 2H), 1.93-2.03 (m, 2H); LRMS (CI, CH$_4$/N$_2$O dep. pos. ion spectrum) m/z (rel. int.) 313 (5), 310 (10), 299 (10), 290 (7), 288 (7), 274 (9), 273 (M+H, 98), 271 (M+H, 100), 231 (10), 229 (9).

C. Methyl 4-(3-(((4-chlorophenyl)methyl)thio)propyl)benzeneacetate

To a solution of p-chlorobenzyl thiol (0.284 ml, 2.15 mmol) in THF (10 ml) was added potassium tert-butoxide (241 mg, 2.15 mmol). After stirring for 10 minutes, Part B bromide (530 mg, 1.95 mmol) in THF (5 ml) was added dropwise. After stirring for 1 hour, the reaction was diluted with 2N NaOH (20 ml) and poured into saturated NaCl (ca. 50 ml). The mixture was extracted with ether (3×75 ml). The combined organic extracts were dried (Na$_2$SO$_4$) and concentrated in vacuo to a solid. Chromatography (flash, silica, 37 mm dia., 20% ethyl acetate/hexanes then 50% acetone/hexanes then 20% methanol/chloroform) yielded title ester (eluting with 20% ethyl acetate/hexanes) and the free acid of title ester (eluting with the other solvents). The free acid was esterified in the usual manner with ethereal diazomethane. Rechromatography of the whole ester product (silica, flash, 25 mm dia., 40% ethyl acetate/hexanes) yielded 334 mg (49%) of title ester as an oil: $^1$H NMR (deuteriochloroform, 60 MHz) $\delta$ 6.87-7.27 (m, 8H), 3.67 (s, 3H), 3.61 (s, 2H), 3.57 (s, 2H), 2.23-2.83 (m, 4H), 1.63-2.05 (m, 2H); Rf (silica, 10% ethyl acetate/hexanes) 0.17.

EXAMPLE 3

Methyl 4-(3-(((4-chlorophenyl)methyl)sulfonyl)propyl)benzeneacetate

Example 2 sulfide 330 mg, 0.946 mmol) was dissolved in methanol (ca. 5 ml) and the solution was cooled below room temperature. A solution of 2KHS0$_5$.KHSO$_4$.K$_2$SO$_4$ (Oxone®) (872 mg, 2.84 mmol of potassium hydrogen persulfate) in water (ca. 5 ml) was added to the cool solution in one portion. After stirring for 30 minutes, the reaction was diluted with 25 ml of water and then extracted with chloroform (4×20 ml). The combined organic extracts were dried (MgSO$_4$) and concentrated in vacuo to yield a solid. This solid was dissolved in a minimum amount of methylene chloride and chromatographed (flash, silica, 50% ethyl acetate/hexanes) to provide 242 mg (67%) of title compound as a white solid: $^1$H NMR (deuteriochloroform, 60 MHz), δ 7.28 (s, 4H), 6.93–7.28 (m, 4H), 3.74 (s, 2H), 3.69 (s, 3H), 3.59 (s, 2H), 2.53–3.03 (m, 4H), 1.69–2.03 (m, 2H).

EXAMPLE 4

4-(3-(((4-Chlorophenyl)methyl)sulfonyl)propyl)benzeneacetic acid

Example 3 ester (240 mg, 0.63 mmol) was dissolved in methanol/methylene chloride (15 ml, 4/3). To the solution was added 2N KOH (2 ml). The mixture was stirred for 2.5 hours and then concentrated in vacuo. The residue was diluted with 20 ml of water and acidified with 1N HCl to bring the pH to 2. The solids were collected by filtration and air dried to yield 224 mg (97%) of a white powder. Recrystallization from ethyl acetate yielded title acid as a white solid: 182 mg (79%); m.p. 211.0°–213.0° C.; $^1$H NMR (deuteriochloroform/tetradeuteriomethanol, 270 MHz) δ 7.32 (Ar Abq, J$_{ab}$=8.4 Hz, v$_{ab}$=17 Hz, 4H), 7.17 (Ar Abq, J$_{ab}$=7.9 Hz, v$_{ab}$=32 Hz, 4H), 4.23 (s, 2H), 3.60 (s, 2H), 2.86–2.92 (m, 2H), 2.70–2.76 (m, 2H), 2.11–2.14 (m, 2H); $^{13}$C NMR deutriochloroform/tetradeuteriomethanol/hexadeuteriodimethyl sulfoxide, complete decoupling, 67.88 MHz) δ 173.2, 138.0, 132.0, 131.4, 128.9, 128.3, 127.9, 125.9, 57.5, 49.8, 40.0, 32.9, 22.7; IR (nujol mull) 1695 (m), 1417 (w), 1404 (w), 1311 (w), 1272 (w), 1252 (w), 1238 (w), 1220 (w), 1183 (w), 1136 (w), 1114 (m), 1093 (w), 1016 (w), 844 (w), 826 (w), 814 (w), 786 (w), 759 (m) cm$^{-1}$; LRMS (CH$_4$/N$_2$O dep. pos. ion spectrum) m/z (rel. int.) 323 (29), 321 (81), 135 (26), 133 (19), 127 (66), 125 (100), 91 (22), 90 (18), 75 (25), 57 (21).

Anal calcd for C$_{18}$H$_{19}$ClO$_4$S.0.14H$_2$O: C, 58.53; H, 5.26; Cl, 9.60; S, 8.68; Found: C, 58.52; H, 5.07; Cl, 9.35; S, 8.92.

EXAMPLE 5

Methyl 4-(3-((4-Methoxyphenyl)thio)propyl)benzeneacetate

To a solution of p-methoxy benzene thiol (394 mg, 2.80 mmol) in THF (30 ml) was added potassium tert-butoxide (315 mg, 2.80 mmol). After 10 minutes, Example 2 Part B bromide (692 mg, 2.55 mmol), dissolved in THF (5 ml), was added dropwise. After 1 hour, the reaction was diluted with 1N NaOH (20 ml) and then extracted with ether (3×50 ml). The combined organic phases were dried (Na$_2$SO$_4$) and concentrated in vacuo to a yellow oil. Chromatography (flash, silica, 37 mm dia., 20% ethyl acetate/hexanes) yielded a white solid: 687 mg (81%); $^1$H NMR (deuteriochloroform, 60 MHz), δ 7.05 (Ar ABq, J$_{ab}$=8.5 Hz, v$_{ab}$=30 Hz, 4H), 7.13 (s, 4H), 3.75 (s, 3H), 3.65 (s, 3H), 3.55 (s, 2H), 2.52–2.95 (m, 4H), 1.68–2.13 (m, 2H).

EXAMPLE 6

Methyl 4-(3-((4-methoxyphenyl)sulfonyl)propyl)benzeneacetate

To a cool solution of Example 5 sulfide (200 mg, 0.605 mmol) in methanol (3.5 ml) was added a solution of Oxone ® (558 mg, 1.82 mmol of potassium hydrogen persulfate) in water (3.5 ml). After stirring for 40 minutes, the reaction was diluted with water (20 ml) and then extracted with chloroform (3×20 ml). The combined organic layers were dried (Na$_2$SO$_4$) and concentrated in vacuo. Chromatography (flash, silica, 15 mm dia., 40% ethyl acetate/hexanes) yielded 191 mg (87%) of title compound as a white solid: $^1$H NMR (deuteriochloroform, 60 MHz) δ 7.75 (d, J=9 Hz, 2H), 6.83–7.27 (m, 6H), 3.85 (s, 3H), 3.67 (s, 3H), 3.57 (s, 2H), 2.83–3.20 (m, 2H), 2.65 (t, J=7 Hz, 2H), 1.77–1.93 (m, 2H).

EXAMPLE 7

4-(3-((4-Methoxyphenyl)sulfonyl)propyl)benzeneacetic acid

To a solution of Example 6 ester (346 mg, 0.955 mmol) in 3/1 methanol/methylene chloride (20 ml) was added 2N KOH (4 ml). After standing for 2 hours, the reaction was concentrated in vacuo to remove the organic solvents. The residue was diluted with water (20 ml) and acidified to pH 2 with 1N HCl. The solid product was collected by filtration, washed with water and then air dried. Recrystallization from ethyl acetate/hexanes yielded title compound in the form of white needles: 298 mg (90%); m.p. 149.0°–150.0° C.; $^1$H NMR (deuteriochloroform/tetradeuteriomethanol, 270 MHz) δ 7.79 (d, J=8.4 Hz, 2H), 7.19 (d, J=8.3 Hz, 2H), 7.00–7.18 (overlapping d, 4H), 3.88 (s, 3H), 3.57 (s, 2H), 3.04–3.09 (m, 2H), 2.64–2.70 (m, 2H), 1.94–2.06 (m, 2H); $^{13}$C NMR (deuteriochloroform/tetradeuteriomethanol, 67.88 MHz, complete decoupling) δ 174.1, 163.7, 138.5, 132.2, 130.1, 130.0, 129.3, 128.3, 114.4, 55.5, 40.5, 33.5, 24.1; IR (nujol mull) 1689 (m), 1600 (w), 1575 (sh), 1493 (sh), 1400 (w), 1282 (w), 1261 (w), 1224 (w), 1202 (w), 1182 (w), 1143 (m), 1117 (w), 1104 (w), 1085 (w), 1018 (w), 831 (w) cm$^{-1}$; LRMS (CH$_4$/N$_2$O dep. pos. ion spectrum) m/z (rel. int.) 377 (22), 367 (20), 366 (100), 350 (15), 349 (74), 331 (10), 320 (10), 303 (19), 58 (8), 51 (9).

Anal Calcd for C$_{18}$H$_{20}$O$_5$S: C, 62.05; H, 5.79; S, 9.20; Found: C, 62.20; H, 5.73; S, 9.45.

EXAMPLE 8

4-(3-((4-Chlorophenyl)sulfonyl)propyl)benzeneacetic acid

A. 2-(4-(3-((4-Chlorophenyl)thio)propyl)phenyl)ethyl alcohol thexyldimethyl silyl ether To a solution of 4-chlorobenzene thiol (1.66 g, 11.4 mmol) in THF (75 ml) was added potassium tert-butoxide (1.28 g, 11.4 mmol) in one portion. After stirring for 10 minutes, Example 2 Part A bromide (4.0 g, 10.4 mmol), dissolved in THF (20 ml), was added dropwise. The reaction was stirred for 2 hours. The reaction was then poured into 1N NaOH (200 ml) and extracted with ether (3×150 ml). The combined organic layers were dried (MgSO$_4$) and concentrated in vacuo to an oil. This material was used crude for subsequent experiments.

B.
2-(4-(3-((4-Chlorophenyl)sulfonyl)propyl)phenyl)ethyl alcohol

To a solution of Part A compound (2.5 g, 5.57 mmol) in 1/1 THF/methanol (60 ml) which had been cooled below room temperature was added a solution of 2KHSO$_5$.KHSO$_4$.K$_2$SO$_4$ (Oxone) (5.13 g, 16.7 mmol of potassium hydrogen persulfate) in water (30 ml). After stirring for 2 hours, the reaction was poured into water (200 ml) and then extracted with chloroform (4×50 ml). The combined extracts were dried (MgSO$_4$) and then concentrated in vacuo to provide 2.49 g of a white solid.

C.
4-(3-((4-Chlorophenyl)sulfonyl)propyl)benzeneacetic acid

To a 0° C. solution of Part B sulfone (2.49 g, 5.17 mmol) in acetone (50 ml) was added, dropwise, freshly prepared Jones reagent (ca. 10 ml. 2.67M). After the addition was complete, the reaction was stirred for 10 minutes. The excess oxidant was quenched with 2-propanol and then the reaction was concentrated in vacuo to remove the organic solvents. Water (150 ml) was added to the residue and the mixture was stirred for 10 minutes. The solid was collected by filtration, air dried and then recrystallized from ethyl acetate/hexanes to yield 1.499 g (81%) of a white solid whose $^1$H and $^{13}$C NMR spectra were identical with those from previously prepared material: m.p. 177°–178° C.

Anal Calcd for C$_{17}$H$_{17}$ClO$_4$S: C, 57.87; H, 4,86; Cl, 10.05; S, 9.09; Found: C, 57.90; H, 4.92; Cl, 9.88; S, 8.83.

EXAMPLE 9
4-(3-((4-t-Butylphenyl)sulfonyl)propyl)benzeneacetic acid

A. 2-(4-(3-((4-t-Butylphenyl)thio)propyl)phenyl)ethyl alcohol thexyldimethylsilyl ether To a stirred solution of 0.33 g of KOtBu (2.95 mmol) in 10 ml of THF was added 0.5 ml of 4-t-butylthiophenol (3.01 mmol) at 23° C. The reaction mixture was stirred for 15 minutes after which time a solution of 0.75 g of 3-[4-(thexyldimethylsilyloxymethyl)phenyl]propyl bromide (1.95 mmol) in 2 ml of THF was added. The reaction mixture was placed in an oil bath and heated to 50° C. for 5.25 hours. The cooled reaction mixture was partitioned between 25 ml each of ether and 1N NaOH solution. The aqueous layer was extracted with 25 ml of ether. The combined ether layers were washed with 25 ml of 1N NaOH solution and dried over MgSO$_4$ overnight. The mixture was filtered and concentrated in vacuo to afford 1.07 g of a colorless oil.

B.
2-(4-(3-((4-t-Butylphenyl)sulfonyl)propyl)phenyl)ethyl alcohol

To a stirred solution of the Part A sulfide in 40 ml each of THF and MeOH was added a solution of 1.66 g Oxone ® (2.7 mmol) in 40 ml of water. The two phase mixture was stirred vigorously for 6 hours. Approximately 10 ml of saturated NaHCO$_3$ solution was added and then the reaction mixture was concentrated in vacuo to a volume of approximately 40 ml. The aqueous residue was acidified to pH 6 and then extracted with 3×50 ml of CHCl$_3$. The combined CHCl$_3$ layers were dried over MgSO$_4$, filtered and concentrated in vacuo to give 0.85 g of crude sulfone.

C.
4-(3-((4-t-Butylphenyl)sulfonyl)propyl)benzeneacetic acid

To a 0° C. solution of the Part B sulfone in 50 ml of acetone was added dropwise Jones reagent until an orange-red color persisted. The reaction mixture was stirred for an additional 15 minutes at 0° C. and then excess oxidant was quenched with isopropyl alcohol (IPA). Solid NaHCO$_3$ was added and the mixture was concentrated in vacuo. The residue was partitioned between 50 ml each of 1N NaOH and ether. The aqueous layer was then acidified to pH=2 with 6N HCl, and extracted with 3×50 ml of CHCl$_3$. The combined CHCl$_3$ layers were dried over MgSO$_4$ filtered and concentrated in vacuo to afford crude title compound. Purification was effected by flash chromatography using 4% CH$_3$OH/CH$_2$Cl$_2$ to afford 190 mg of title acid as eluent.

EXAMPLE 10
4-(3-((2-Naphthyl)sulfonyl)propyl)benzeneacetic acid

A. 2-(4-(3-((2-Naphthyl)thio)propyl)phenyl)ethyl alcohol thexyldimethyl silyl ether To a stirred solution of 0.33 of KOtBu (2.95 mmol) in 10 ml of THF was added 0.47 g of 2-naphthylmercaptan (3.0 mmol) at 23° C. The reaction mixture became extremely thick so an additional 5 ml of THF was added. The resulting thick slurry was stirred for 15 minutes after which time a solution of 0.75 g of 3-[4-(2-(thexyldimethylsilyloxymethyl))phenyl]propyl bromide (1.95 mmol) in 2 ml of THF was added. The reaction mixture was placed in an oil bath and heated to 50° C. for 5.25 hours. The cooled reaction mixture was partitioned between 25 ml each of ether and 1N NaOH soluiton. The aqueous layer was extracted with 25 ml of ether. The combined ether layers were washed with 25 ml of 1N NaOH solution and dried over MgSO$_4$ overnight. The mixture was filtered and concentrated in vacuo to afford 0.95 g of a colorless oil.

B. 2-(4-(3-((2-Naphthyl)sulfonyl)propyl)phenyl)ethyl alcohol

To a stirred solution of the Part A sulfide in 40 ml each of THF and MeOH was added a solution of 1.66 g Oxone (2.7 mmol) in 40 ml of water. The two phase mixture was stirred vigorously for 6 hours. Approximately 10 ml of saturated NaHCO$_3$ solution was added and then the reaction mixture was concentrated in vacuo to a volume of approximately 40 ml. The aqueous residue was acidified to pH 6 and then extracted with 3×50 ml of CHCl$_3$. The combined CHCl$_3$ layers were dried over MgSO$_4$, filtered and concentrated in vacuo to give 0.75 g of crude sulfone.

C. 4-(3-((2-Naphthyl)sulfonyl)propyl)benzenacetic acid

To a 0° C. solution of the Part B sulfone in 50 ml of acetone was added dropwise Jones reagent until an orange-red color persisted. The reaction mixture was stirred for an additional 15 minutes at 0° C. and then excess oxidant was quenched with isopropyl alcohol (IPA). Solid NaHCO$_3$ was added and the mixture was concentrated in vacuo. The residue was partitioned between 50 ml each of 1N NaOH and ether. The aqueous layer was then acidified to pH=2 with 6N HCl, and extracted with 3×50 ml of CHCl₃. The combined CHCl₃ layers were dried over MgSO₄, filtered and concentrated in vacuo to afford crude title compound. Crude product was recrystallized from ether-chloroform to afford 260 mg title acid. A second recrystallization from chloroform afforded 170 mg pure title acid.

EXAMPLE 11

4-(3-((4-Chlorophenyl)sulfinyl)propyl)benzeneacetic acid

To a 0° C. solution of Example 8 Part A sulfide (500 mg, 1.11 mmol) in acetone (6 ml) was added, dropwise, freshly prepared Jones reagent (2.67M, ca. 1.2 ml). After stirring for 40 minutes, the reaction was quenched with 2-propanol and then concentrated in vacuo. The residue was then stirred with water (50 ml) for 30 minutes at which time a yellow solid had formed. The solid was collected by filtration, washed with water and air dried. Chromatography (flash, silica, 25 mm dia., ethyl acetate then 20% methanol/chloroform) provided a white solid. The solid was then triturated with 2 portions of hot ethyl acetate (ca. 10 ml each) leaving the desired sulfoxide as white amorphous solid: ¹H NMR (tetradeuteriomethanol, 270 MHz) δ 7.53–7.62 (m, 4H), 7.02–7.19 (m, 4H), 3.46 (s, 2H), 2.55–2.95 (m, 4H), 1.75–2.00 (m, 2H); ¹³C NMR (tetradeuteriomethanol, 67.88 MHz, complete decoupling) δ 178.3, 142.4, 139.9, 138.3, 134.9, 130.6, 130.5, 129.4, 127.0, 56.4, 43.1.

EXAMPLE 11A 4-(3-((4-Chlorophenyl)thio)propyl)benzeneacetic acid

A. Methyl 4-(3-((4-chlorophenyl)thio)propyl)benzeneacetate

To a solution of p-chlorobenzene thiol (313 mg, 2.16 mmol) in THF (20 ml) was added potassium t-butoxide (243 mg, 2.16 mmol). After stirring for 5 minutes, a solution of crude Example 2 Part B bromide (587 mg) in THF (5 ml) was added dropwise. The reaction was stirred for 18 hours. The reaction was diluted with 1N NaOH (50 ml) and then extracted with ether (3×20 ml). The combined organic extracts were dried (MgSO₄) and concentrated in vacuo to an oil. Chromatography (flash, silica, 37 mm dia., 20% ethyl acetate/hexanes) provided title ester (320 mg): ¹H NMR (deuteriochloroform, 60 MHz) δ 6.93–7.30 (m, 8H), 3.65 (s, 3H), 3.57 (s, 2H), 2.50–3.00 (m, 4H), 1.57–2.17 (m, 2H); R_f (silica, 25% ethyl acetate/hexanes) 0.42.

B. 4-(3-((4-Chlorophenyl)thio)propyl)benzeneacetic acid

Part A ester (315 mg, 0.941 mmol) was dissolved in methanol (8 ml). To this solution was added 2N KOH (2 ml) which caused a precipitate to form. Methylene chloride (ca. 4 ml) was added to create a homogeneous solution. After TLC monitoring indicated consumption of starting material, the reaction was concentrated in vacuo to removed organic solvents. To the residue was added 20 ml of water and then 1N HCl to bring the pH to 2. The solid which precipitated was collected by filtration, washed with water and air dried. Chromatography (flash, 15 mm dia. silica, 10% methanol/chloroform) provided a white solid which was recrystallized from benzene/hexanes to provide white crystals: 182 mg (58%); m.p. 94°–96° C.; R_f (silica, 10% methanol/chloroform) 0.46 ¹H NMR (deuteriochloroform, 270 MHz) δ 8.1–9.8 (v br s, 1H), 7.10–7.24 (m, 8H), 3.61 (s, 2H), 2.87 (t, J=7 Hz, 2H), 2.71 (t, J=7 Hz, 2H), 1.92 (quint, J=7 Hz, 2H); ¹³C NMR (deuteriochloroform, 67.88 MHz, complete decoupling) δ 177.6, 140.2, 135.0, 131.9, 131.0, 130.5, 129.4, 128.9, 128.7, 40.6, 34.2, 33.1, 30.4; IR(mull) 1686 (s), 1511 (w), 1393 (w), 1325 (w), 1277 (w), 1229 (m), 1199 (m), 1092 (m), 1042 (w), 1019 (w), 1008 (m), 927 (m), 824 (m), 818 (w), 805 (m), 781 (w), 747 (w), 668 (w) cm⁻¹; LRMS (CI, CH₄/N₂O dep, pos. ion spectrum)m/z (rel. int.) 324 (7), 323 (38), 322 (29), 321 (100), 320 (28), 275 (5).

Anal Calcd for $C_{17}H_{17}SO_2Cl \cdot 0.12H_2O$: C, 63.21; H, 5.38; Cl, 10.97; S, 9.92; Found: C, 63.18; H, 5.18; Cl, 11.06; S, 9.88.

EXAMPLES 12 TO 23

Following the procedure of Example 1 except substituting for Example 1 part A bromide the bromoalkyl benzene compound shown in Column II of Table I set out below and substituting for (4-chlorophenyl)methylsulfone, the sulfone shown in Column I, the product shown in Column III is obtained.

It will be appreciated that wherein the Ar group in the starting materials shown in Column I includes substituents that include acidic hydrogens such as OH or primary or secondary amine then these starting materials will be reacted with a protecting compound such as set out hereinbefore with respect to "Pro" and the Pro group will be removed as a final step as described above.

| Ex. No. | Ar | $(CH_2)_{p-1}$ | (position)-$(CH_2)_q$—A—$(CH_2)_r$— |
|---|---|---|---|
|  | Column I $\underset{Ar-S-CH_3}{\overset{O\phantom{/}\,\,O}{\diagdown\!\!\diagup}}$ | Column II Br—$(CH_2)_{p-1}$—⟨benzene ring positions 1,2,3,4⟩—$(CH_2)_q$—A—$(CH_2)_r$— | |
| 12. | 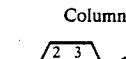 | $\underset{-CH_3-CH-}{\overset{CH_3}{|}}$ | (4)- $CH_2$—$(CH_2)_2$— |
| 13. |  | —$CH_2$—$CH_2$— | (3)- —$CH_2$—$CH=CH$—$CH_2$— |

-continued

| Ex. No. | Ar | (CH₂)$_{p-1}$ | (position)-(CH₂)$_q$—A—(CH₂)$_r$— |
|---|---|---|---|
| 14. | 4-F-C₆H₄— | —CH₂—C(H)(CH₃)—CH(CH₃)— | (2)- —CH=CH— |
| 15. | 3-HO-C₆H₄— | —CH(C₂H₅)— | (4)- —CH₂—CH₂— |
| 16. | 4-CH₃O-C₆H₄— | —CH₂—CH₂—CH(CH₃)—CH₂— | (4)- —CH₂— |
| 17. | 6-CH₃-naphth-2-yl | —CH(CH₃)—CH(CH₃)— | (3)- —CH=CH—CH₂— |
| 18. | 4-biphenyl | —CH(CH₃)—CH(OCH₃)— | (2)- —C(CH₃)=CH— |
| 19. | 4-C₄H₉-C₆H₄— | —(CH₂)₃— | (4)- —CH₂—C(CH₃)=C(CH₃)—CH₂— |
| 20. | 4'-CH₃O-biphenyl-4-yl | —CH₂—CH(CH₃)—CH(CH₃)— | (3)- —CH(C₂H₅)—CH₂— |
| 21. | 3-(CH₃—NH)-C₆H₄— | CH₂ | (4)- —CH(OCH₃)—CH(OCH₃)— |
| 22. | 4-C₃H₇-C₆H₄— | CH₂ | (3)- —CH(OCH₃)— |
| 23. | 4-(C₂H₅NH)-C₆H₄— | CH₂—CH₂ | (2)- —CH₂CH₂— |

Column III

Ar—S(O)₂—(CH₂)$_{p-1}$—CH₂—C₆H₄—(CH₂)$_q$—A—(CH₂)$_r$—COOH

| 12. | Same as Col. I | | Same as Col. II |
| 13. | | | |
| 14. | | | |
| 15. | | | |
| 16. | | | |

-continued

| Ex. No. | Ar | $(CH_2)_{p-1}$ | (position)-$(CH_2)_q$—A—$(CH_2)_r$— |
|---|---|---|---|
| 17. | | | |
| 18. | | | |
| 19. | | | |
| 20. | | | |
| 21. | | | |
| 22. | | | |
| 23. | | | |

EXAMPLES 34 TO 35

Following the procedure of Example 2 except substituting for p-chlorobenzenemercaptan, the mercaptan shown in Column I of Table II set out below and substituting for the bromoalkylenebenzene carboxylic acid ester, the compound shown in Column II, the product shown in Column III is produced.

| Ex. No. | Ar | $(CH_2)_m$ | $(CH_2)_p$ | (position)-$(CH_2)_q$—A—$(CH_2)_r$— |
|---|---|---|---|---|
| | Column I: Ar—$(CH_2)_m$—SH | | Column II: Br—$(CH_2)_p$—C$_6$H$_4$—$(CH_2)_q$—A—$(CH_2)_r$—COOCH$_3$ | |
| 24. | phenyl | — | —CH$_3$—CH(CH$_3$)— | (4)- CH$_2$—(CH$_2$)$_2$— |
| 25. | 2-naphthyl | CH$_2$ | —CH$_2$—CH$_2$— | (3)- —CH$_2$—CH=CH—CH$_2$— |
| 26. | 4-fluorophenyl | $(CH_2)_2$ | —CH$_2$—C(H)(CH$_3$)—CH(CH$_3$)— | (2)- —CH=CH— |
| 27. | 3-hydroxyphenyl | $(CH_2)_3$ | —CH(C$_2$H$_5$)— | (4)- —CH$_2$—CH$_2$— |
| 28. | 4-methoxyphenyl | —CH(CH$_3$)— | —CH$_2$—CH$_2$—CH(CH$_3$)—CH$_2$— | (4)- —CH$_2$— |
| 29. | 6-methyl-2-naphthyl | —CH(CH$_3$)—CH(CH$_3$)— | —CH(CH$_3$)—CH(CH$_3$)— | (3)- —CH=CH—CH$_2$— |
| 30. | 4-biphenyl | —CH$_2$—CH(CH$_3$)— | —CH(CH$_3$)—CH(OCH$_3$)— | (2)- —C(CH$_3$)=CH— |
| 31. | 4-acetylphenyl (CH$_3$—CO—) | CH$_2$ | —(CH$_2$)$_3$— | (4)- —CH$_2$—C(CH$_3$)=C(CH$_3$)—CH$_2$— |

-continued

| Ex. No. | Ar | (CH₂)ₘ | (CH₂)ₚ | (position)-(CH₂)_q—A—(CH₂)_r— |
|---|---|---|---|---|
| 32. | ![benzoyl-phenyl] | — | $-CH_2-\underset{CH_3}{\overset{|}{CH}}-\underset{CH_3}{\overset{|}{CH}}-$ | (3)- $-\underset{C_2H_5}{\overset{|}{CH}}-CH_2-$ |
| 33. | CH₃NH—⌬— | $-\underset{CH_3}{\overset{|}{CH}}-CH_2-$ | CH₂ | (4)- $-\underset{OCH_3}{\overset{|}{CH}}-\underset{OCH_3}{\overset{|}{CH}}-$ |
| 34. | CH₃C(O)—⌬— | —CH₂— | CH₂ | (3)- $-\underset{OCH_3}{\overset{|}{CH}}-$ |
| 35. | HOOC—⌬— | $-\underset{C_2H_5}{\overset{|}{CH}}-$ | CH₂CH₂ | (2)- —CH₂CH₂— |

Column III

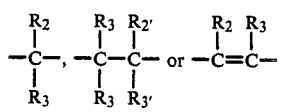

| | | |
|---|---|---|
| 24. | Same as Col. I | Same as Col. II |
| 25. | | |
| 26. | | |
| 27. | | |
| 28. | | |
| 29. | | |
| 30. | | |
| 31. | | |
| 32. | | |
| 33. | | |
| 34. | | |
| 35. | | |

EXAMPLES 36 TO 47

Following the procedure of Example 3 except substituting for the sulfide of Example 2, the sulfides of Examples 17 to 28, the corresponding sulfones are obtained.

EXAMPLES 48 TO 59

Sulfoxide Preparation

Following the procedure for Example 11 except substituting for the sulfide of Example 8 Part A, the sulfides of Examples 36 to 47, followed by hydrolysis, the corresponding sulfoxides are obtained.

What is claimed is:

1. A compound having the structure

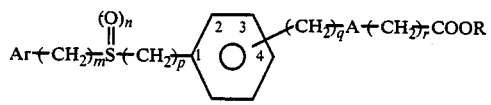

wherein Ar is an aryl group which is unsubstituted or substituted with one or more of halogen, lower alkyl, lower alkoxy, phenyl, hydroxy, alkanoyl, aroyl, alkylamino, alkoxycarbonyl or carboxy;

A is $$-\underset{R_3}{\overset{R_2}{\overset{|}{\underset{|}{C}}}}-, \quad -\underset{R_3}{\overset{R_2}{\overset{|}{\underset{|}{C}}}}-\underset{R_{3'}}{\overset{R_{2'}}{\overset{|}{\underset{|}{C}}}}- \quad \text{or} \quad -\underset{}{\overset{R_2}{\overset{|}{C}}}=\underset{}{\overset{R_3}{\overset{|}{C}}}-$$

wherein $R_2$ and $R_3$, and $R_{2'}$ and $R_{3'}$ may be the same or different and are independently selected from hydrogen or lower alkyl;

R is hydrogen, alkali metal or lower alkyl;

n is 0, 1, or 2;

m is 0, 1, 2, or 3;

p is 1 to 5;

q is 0, 1, 2 or 3;

r is 0, 1, 2, or 3;

and the $(CH_2)_m$, $(CH_2)_p$, $(CH_2)_q$ and/or $(CH_2)_r$ groups may be unsubstituted or optionally substituted with one or two lower alkyl groups and/or are one or two lower alkoxy groups, the term lower alkyl or alkyl by itself or as part of another group is unsubstituted or may be substituted with one or two halo-substituents, alkoxy, aryl, alkylaryl, haloaryl, cycloalkyl or alkylcycloalkyl.

2. The compound as defined in claim 1 wherein n is 2.
3. The compound as defined in claim 1 wherein n is 1.
4. The compound as defined in claim 1 wherein n is 2, m is 0, Ar is a substituted phenyl.
5. The compound as defined in claim 4 wherein —(CH$_2$)$_q$—A—(CH$_2$)$_r$— is in the 4-position and represents —CH$_2$—, —CH$_2$CH$_2$— or —CH=CH—.
6. The compound as defined in claim 1 having the name 4-(3-((4-chlorophenyl)sulfonyl)propyl)benzeneacetic acid.
7. The compound as defined in claim 1 having the name methyl 4-(3-((4-chlorophenyl)thio)propyl)benzeneacetate.
8. The compound as defined in claim 1 having the name methyl 4-(3-((4-chlorophenyl)sulfonyl)propyl)benzeneacetate.
9. The compound as defined in claim 1 having the name 4-(3-((4-chlorophenyl)thio)propyl)benzeneacetic acid.
10. The compound as defined in claim 1 having the name methyl 4-(3-(((4-chlorophenyl)methyl)thio)propyl)benzeneacetate, methyl 4-(3-(((4-chlorophenyl)methyl)sulfonyl)propyl)benzeneacetate or 4-(3-(((4-chlorophenyl)methyl)sulfonyl)propyl)benzeneacetic acid.
11. The compound as defined in claim 1 having the name methyl 4-(3-((4-methoxyphenyl)thio)propyl)benzeneacetate, methyl 4-(3-((4-methoxyphenyl)sulfonyl)propyl)benzeneacetate or 4-(3-((4-methoxyphenyl)sulfonyl)propyl)benzeneacetic acid.
12. The compound as defined in claim 1 having the name 4-(3-((4-t-butylphenyl)sulfonyl)propyl)benzeneacetic acid or 4-(3-(2-naphthyl)sulfonyl)propyl)benzeneacetic acid.
13. A method of inhibiting arachidonic acid-induced platelet aggregation, which comprises administering to the circulatory system of a mammalian host an effective amount of a compound as defined in claim 1 or a pharmaceutically acceptable salt thereof.
14. The method as defined in claim 13 wherein said compound is administered in an amount within the range of from about 0.1 to about 100 mg/kg.
15. A composition for inhibiting arachidonic acid-induced platelet aggregation or bronchoconstriction comprising an effective amount of a compound as defined in claim 1 or a pharmaceutically acceptable salt thereof, and a pharmaceutically acceptable carrier therefor.
16. A method of inhibiting platelet aggregation which comprises administering to a mammalian host an effective amount of a compound as defined in claim 1 or a pharmaceutically acceptable salt thereof.
17. A method of inhibiting bronchoconstriction associated with asthma, which comprises administering to a mammalian host an effective amount of a compound as defined in claim 1 or a pharmaceutically acceptable salt thereof.
18. A method of treating peripheral vascular diseases, which comprises topically or systemically administering to a mammalian host an effective amount of a compound as defined in claim 1 or a pharmaceutically acceptable salt thereof.
19. A method of inhibiting bronchoconstriction, which comprises administering to a mammalian host an effective amount of a compound as defined in claim 1 or a pharmaceutically acceptable salt thereof.

* * * * *